United States Patent [19]

Takayanagi et al.

[11] Patent Number: 5,399,724
[45] Date of Patent: Mar. 21, 1995

[54] ACYCLIC TERPENE COMPOUND

[75] Inventors: Hisao Takayanagi; Yasunori Kitano, both of Yokohama; Yasuhiro Morinaka, Tsuchiura, all of Japan

[73] Assignee: Mitsubishi Kasei Corporation, Tokyo, Japan

[21] Appl. No.: 128,266

[22] Filed: Sep. 28, 1993

Related U.S. Application Data

[63] Continuation of Ser. No. 982,042, Nov. 25, 1992, abandoned, which is a continuation of Ser. No. 730,771, Jul. 26, 1991, abandoned.

[30] Foreign Application Priority Data

Nov. 29, 1989 [JP] Japan .................. 1-309796

[51] Int. Cl.$^6$ .............. C07D 309/12; C07D 307/20; C07D 57/02
[52] U.S. Cl. .................. 549/420; 549/498; 549/499; 554/219; 554/121; 554/116; 560/262; 560/113; 568/496
[58] Field of Search ............... 568/496; 560/262, 113; 554/219, 121, 116; 549/420, 498, 499

[56] References Cited

U.S. PATENT DOCUMENTS 4,059,641 11/1977 Mishima et al. .............. 560/113

FOREIGN PATENT DOCUMENTS 2068370 8/1981 United Kingdom .

OTHER PUBLICATIONS

Inoue et al., J.C.S., Chem. Commun., 1036–37 (1987).
McMurry et al., Tet. Lett., 30(10), pp. 1173–1176 (1989).
Vig et al., Indian Journal of Chemistry, vol. 24B, pp. 513–515 (1985).

*Primary Examiner*—Nicky Chan
*Attorney, Agent, or Firm*—Wenderoth, Lind & Ponack

[57] ABSTRACT

Novel acyclic terpene compounds useful as intermediates for producing sarcophytol A which have an anti-carcinogenic promotor activity and anti-tumor activity, which compounds are shown by the following general formula (I):

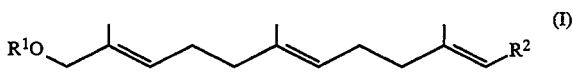

[wherein $R^1$ is a hydrogen atom, 1-alkoxyalkyl group, tetrahydrofuryl group, tetrahydropyranyl group or acyl group; $R^2$ is a group of formula: —CHO, —CH$_2$OR$^3$ or

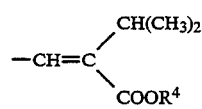

(wherein $R^3$ is a hydrogen atom, 1-alkoxyalkyl group, tetrahydrofuryl group, tetrahydropyranyl group or acyl group; and $R^4$ is C$_1$ to C$_4$ alkyl group) with the proviso that $R^1$ and $R^3$ do not represent the same substituents simultaneously; when $R^1$ is a hydrogen atom, $R^3$ is not acetyl group or tetrahydropyranyl group; and when $R^2$ is a group of formula:

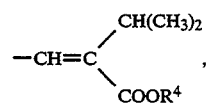

$R^1$ is not a hydrogen atom).

1 Claim, No Drawings

ACYCLIC TERPENE COMPOUND

This application is a continuation of now abandoned application Ser. No. 07/982,042, filed Nov. 25, 1992, abandoned, which is a continuation of now abandoned application, Ser. No. 07/730,771, filed Jul. 26, 1991, abandoned.

FIELD OF THE ART

The present invention relates to novel acyclic terpene compounds. More particularly, the present invention is directed to substituted-acyclic terpene compounds useful as intermediates for producing sarcophytol A which have an anti-carcinogenic promotor activity and anti-tumor activity.

BACKGROUND OF THE INVENTION

The sarcophytol A was reported to exhibit anti-carcinogenic promotor activity [Cancer Surveys, 2, 540 (1983); Taisha, Vol. 25, Special Edition, Gan '88,3 (1988)] and anti-tumor activity [Japanese Patent Publication 20213/1988], whereby it has been regarded as a useful anti-tumor agent. As can be seen from the following structure, sarcophytol A is a cembrane type diterpene-alcohol containing one conjugated double bond and two other double bonds in the 14-membered ring.

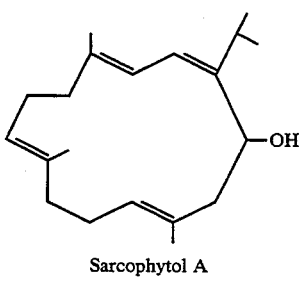

Sarcophytol A

The present inventors studied with the aim of developing a synthetic method of sarcophytol A and have proposed a synthetic route shown by the following synthetic route 1 [JP Patent Appln. 181710/1989; filing date: Jul. 14, 1989].

Synthetic Route 1

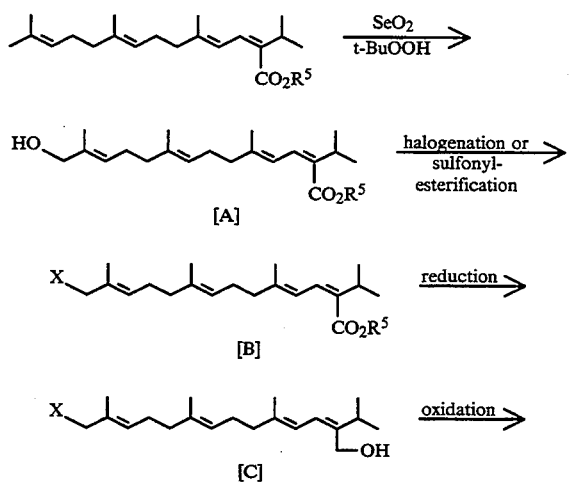

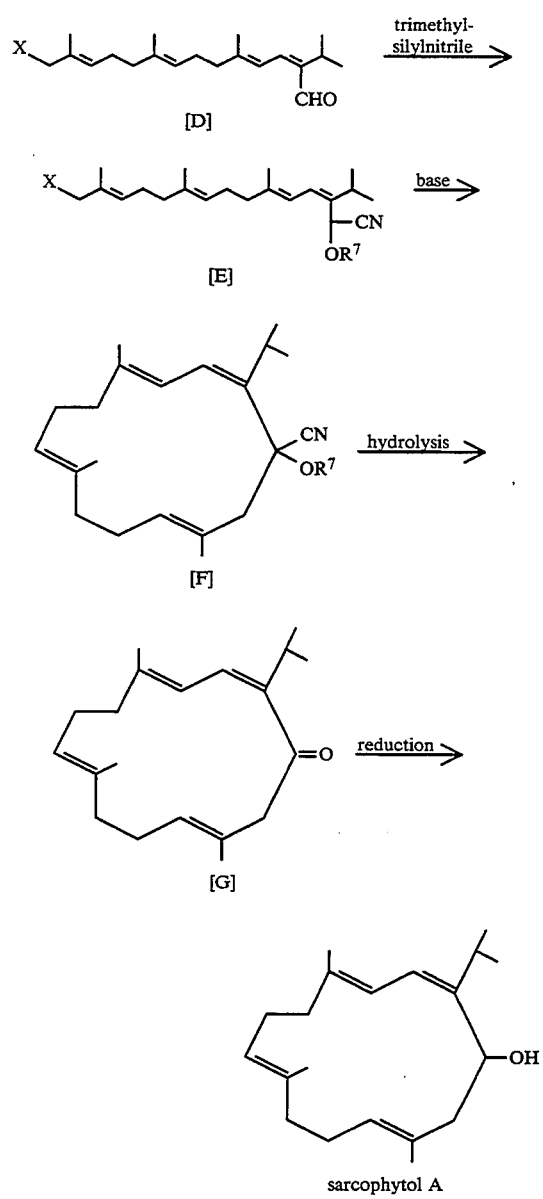

wherein $R^5$ is $C_1$ - $C_4$ lower alkyl group or phenyl group; X is a halogen atom or a leaving group such as $OSO_2R^6$ and the like; and $R^7$ is a hydrogen atom, trimethylsilyl group or 1-ethoxyethyl group.

The process according to the above synthetic route 1 requires as the starting material a valuable compound having entire carbon atoms and structure essential for the production of sarcophytol A and comprises an oxidation of the terminal methyl group of said starting compound with selenium dioxide. However, since the oxidation at the terminal position is poor in the selectivity and yield, said process was not satisfactory for the industrial application.

Under these circumstances, the present inventors have investigated earnestly with the aim of developing an improved method for producing the intermediate [A] effectively and easily, thereby providing a process applicable to the industrial production of the final product, sarcophytol A, and have now found certain novel acyclic terpene compounds useful for the establishment of the purpose of the invention.

DISCLOSURE OF THE INVENTION

The present invention provides acyclic terpene compounds of the general formula (I):

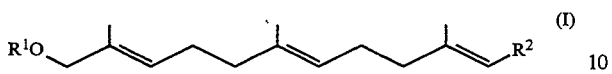

[wherein $R^1$ is a hydrogen atom, 1-alkoxyalkyl group, tetrahydrofuryl group, tetrahydropyranyl group or carboxylic acyl group; $R^2$ is a group of formula: —CHO, —CH$_2$OR$^3$ or

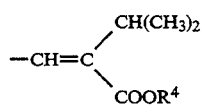

(wherein $R^3$ is a hydrogen atom, 1-alkoxyalkyl group, tetrahydrofuryl group or tetrahydropyranyl group, and $R^4$ is $C_1$ to $C_4$ alkyl group) with the proviso that $R^1$ and $R^3$ do not represent the same substituents simultaneously; when $R^1$ is a hydrogen atom, $R^3$ is not a tetrahydropyranyl group; and when $R^2$ is a group of formula:

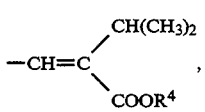

$R^1$ is not a hydrogen atom].

The terms used for the definition of the compound (I) are explained below.

In the definition of $R^1$ and $R^3$, examples of "1-alkoxyalkyl group" include methoxymethyl group, 2-ethoxyethyl group and 1-n-butoxyethyl group and the like.

Examples of "carboxylic acyl group" include acetyl group, benzoyl group and the like.

In the definition of $R^4$, examples of "$C_1$ to $C_4$ lower alkyl group" include a straight or branched alkyl group containing 1 to 4 carbon atoms, for example, methyl group, ethyl group, n-propyl group, isopropyl group and the like.

PREFERRED EMBODIMENT OF THE INVENTION

Typical compounds represented by the general formula (I) are shown below. However, these are given for illustrative purpose only, and never to restrict the scope of the invention.

TABLE 1

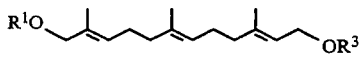

| Compound No. | $R^1$ | $R^3$ |
|---|---|---|
| 1 | —CH$_2$OMe | —COCH$_3$ |
| 2 | —CHCH$_3$(OC$_2$H$_5$) | —COCH$_3$ |
| 3 | 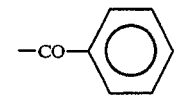 | —COCH$_3$ |

TABLE 1-continued

| Compound No. | $R^1$ | $R^3$ |
|---|---|---|
| 4 | —H | 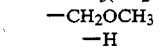 |
| 5 | —H | —CHCH$_3$(OC$_2$H$_5$) |
| 6 | —H | —CH$_2$OCH$_3$ |
| 7 | —CHCH$_3$(OC$_2$H$_5$) | —H |
| 8 | 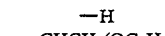 | —H |
| 9 | —COCH$_3$ | —CHCH$_3$(OC$_2$H$_5$) |
| 10 | 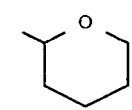 |  |
| 11 | —COCH$_3$ | —H |
| 12 |  | —H |
| 13 | —CH$_2$OCH$_3$ | —H |

TABLE 2

| Compound No. | $R^1$ |
|---|---|
| 14 | —H |
| 15 | —CH$_2$OCH$_3$ |
| 16 | —CHCH$_3$(OC$_2$H$_5$) |
| 17 | 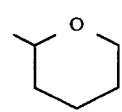 |
| 18 | —COCH$_3$ |
| 19 | 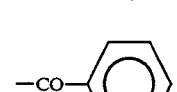 |

TABLE 3

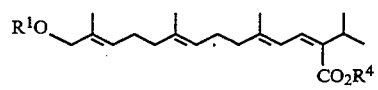

| Compound No. | $R^1$ | $R^4$ |
|---|---|---|
| 20 | —CH$_2$OCH$_3$ | —C$_2$H$_5$ |
| 21 | —CHCH$_3$(OC$_2$H$_5$) | —C$_2$H$_5$ |

TABLE 3-continued

R¹O~~~~CO₂R⁴ (structure)

| Compound No. | R¹ | R⁴ |
|---|---|---|
| 22 | (tetrahydropyranyl group) | —C₂H₅ |
| 23 | —COCH₃ | —CH₃ |
| 24 | —CO—(phenyl) | —CH₃ |

All the above compounds and others of formula (I) are useful as intermediates for the production of sarcophytol A.

Production of the compounds of the present invention is described below according to the type of the compound. As one of skill in the art will appreciate, the present invention is not restricted to compounds produced by the methods herein disclosed, but it include any compounds of formula (I) which can be produced by other methods known to those skilled in the art.

(1) Compound wherein $R^1$ is 1-alkoxyalkyl group and $R^2$ is $CH_2OR^3$ ($R^3$ is acyl group)

Compounds of this type can be produced using, as a starting material, a known compound such as 12-hydroxyfarnesylacetate [Tetrahedron 43, 5499(1987)] or 12-hydroxyfarnesyl ester which is formed at the corresponding acyl group of farnesol in a similar manner. Thus, either of above starting compound is reacted with 0.5 to 10 mol equivalent of a vinyl ether such as ethylvinyl ether, dihydropyrane or the like in the presence of a catalytic amount of an acid, for example, a mineral acid such as hydrochloric acid, sulfuric acid or the like, an organic sulfonic acid such as p-toluenesulfonic acid, camphor-sulfonic acid or the like, or a salt of a strong acid such as p-toluenesulfonic acid pyridinium salt or the like at temperature from about −20° to about 100 ° C. in an appropriate solvent, for example, a halogen solvent such as methylene chloride, chloroform or the like, or an eher solvent such as diethyl ether, tetrahydrofuran or the like or ethyl acetate.

Alternatively, either of above-mentioned starting material is reacted with 0.5 to 10 mol equivalent of a 1-haloalkyl ether such as chloromethylmethyl ether, chloromethyl-2-methoxyethyl ether or the like in the presence of 0.5 to 10 mol equivalent of a base, for example, a metal hydride such as sodium hydride, potassium hydride or the like, amines such as triethylamine, pyridine, diisopropylamine or the like at temperature from about −20° to about 100 ° C. in an appropriate solvent such as tetrahydrofuran, diethyl ether, dimethylformamide or the like, or without solvent.

(2) Compound (I) wherein $R^1$ is a hydrogen atom and $R_2$ is $CH_2OR^3$ ($R^3$ is 1-alkoxyalkyl group)

Compounds of this type can be produced by, for example, reacting a corresponding 1-alkoxyalkyl ether of farnesol, which can be prepared from farnesol in the similar manner as above (1), with 1 to 50 mol equivalent of t-butylhydroxyperoxide in the presence of 0.01 to 0.1 mol equivalent of selenium dioxide at temperature from about −20° to about 50 ° C. over a period of 1 to 100 hours.

(3) Compound (I) wherein $R^1$ is acyl group; and $R^2$ is $CH_2OR^3$ ($R^3$ is 1-alkoxyalkyl group)

Compounds of this type can be produced by reacting a compound prepared in the above (2) with an equivalent amount to 10 mol equivalent of an acyl halide such as acetyl chloride, benzoyl chloride or the like, or acid anhydride such as acetic anhydride, trichloroacetic anhydride or the like in the presence of 1 to 10 mol equivalent of a base such as triethylamine, pyridine or the like at temperature from about −20° to about 100 ° C. in a halogen solvent such as dichloromethane, chloroform or the like, an ether solvent such as diethyl ether, tetrahydrofuran or the like, hydrocarbon solvent such as benzene, toluene, n-hexane or the like, or without solvent where the base serves as a solvent.

(4) Compound (I) wherein $R^1$ is 1-alkoxyalkyl group and $R^2$ is $CH_2OH$

Compounds of this type can be prepared by subjecting a compound obtained in the above (1) to the following process.

a) Ester exchange

A compound is treated with a catalytic amount to 2 mol equivalent of metal alkoxide at temperature from about −50° to about 50° C. in a solvent such as methanol, ethanol or the like.

b) Hydrolysis

A compound is treated with 0.5 to 10 mol equivalent of aqueous sodium hydroxide, potassium hydroxide or the like at temperature from about −50° to about 50° C. in a solvent such as methanol, ethanol, tetrahydrofuran or the like.

c) Reduction

A compound is treated with 0.5 to 10 mol equivalent of a metal-hydrogen complex such as lithium aluminium hydride or the like, or a metal hydride such as diisobutylaluminium hydride or the like at temperature from about −70° to about 50° C. in a solvent such as diethyl ether, THF, n-hexane, toluene or the like.

(5) Compound (I) wherein $R^1$ is acyl group and $R^2$ is $CH_2OH$

Compounds of this type can be produced by treating a compound prepared in the above (3) with a catalytic amount to 0.5 mol equivalent of a mineral acid such as hydrochloric acid, sulfuric acid or the like, an organic strong acid such as p-toluenesulfonic acid or the like, or a salt of a strong acid such as p-toluenesulfonic acid pyridinium salt or the like in an appropriate solvent such as methanol, ethanol or the like to remove only the 1-alkoxyalkyl group therefrom.

(6) Compound (I) wherein $R^1$ is 1-alkoxyalkyl group or acyl group and $R^2$ is CHO Compounds of this type can be prepared by treating a compound obtained in the above (4) or (5) with 5 to 20 times by weight of a oxidizing agent such as powdered manganese dioxide, barium manganate or the like at temperature from about −50° to about 50° C. over a period of 1 to 50 hours in a solvent, for example, a halogen solvent such as methylene chloride, chloroform or the like, a hydrocarbon solvent such as hexane, heptane or the like, ethyl ether, or ethyl acetate.

(7) Compound (I) wherein $R^1$ is a hydrogen atom and $R^2$ is CHO

Compounds of this type can be produced by treating a compound (I) wherein $R^1$ is 1-alkoxyalkyl group obtained in the above (6) with 0.1 to 12 N mineral acid such as hydrochloric acid, sulfuric acid or the like, an organic strong acid such as p-toluenesulfonic acid or the like, or p-toluenesulfonic acid pyridinium salt or the like at temperature from about 0° C. to room temperature over a period of 5 minutes to room temperature in a solvent such as aqueous tetrahydrofuran, methanol or the like.

(8) Compound (I) wherein $R^2$ is

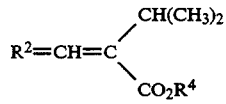

wherein $R^4$ is as defined above.

Compounds of this type can be prepared, for example, by treating a compound obtained in the above (6) or (7) with an anion at temperature from about $-100°$ to about 100° C. in a an ether solvent such as tetrahydrofuran, ethyl ether or the like, an aprotic polar solvent such as dimethylformamide or the like. The anion can be generated and provided by reacting 1 to 10 mol equivalent of Wittig-Horner reagent such as ethyl 2-(diethylphosphono)-3-methyl-butanate, methyl 2-(dimethylphosphono)isovaleronitrile or the like with 0.1 to 10 mol equivalent (for the Wittig-Horner reagent) of a base such as metal hydride (e.g. sodium hydride, potassium hydride), organic metal (e.g. n-butyllithium, lithium diisopropylamide) or metal alkoxide (e.g. sodium methoxide, potassium t-butoxide).

As will hereinafter be described in detail, the compound [A], an intermediate of the above-mentioned synthetic route 1 of sarcophytol A, can be prepared efficiently using the compound of formula (I) as a starting material, avoiding the oxidation with selenium dioxide of the existent method.

The production of the intermediate compound [A] from the compound (I) can be illustrated by the following synthetic route shown below.

Synthetic Route of Compound [A]

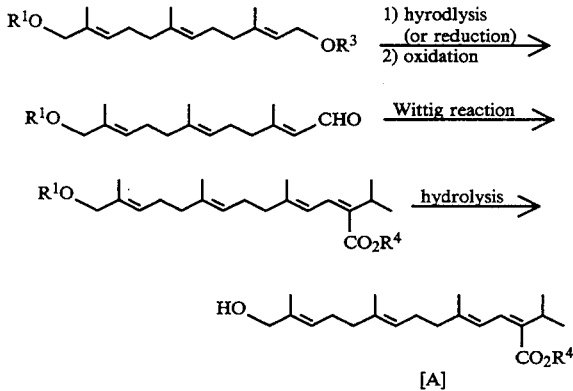

wherein $R^1$, $R^3$, and $R^4$ are as defined above.

According to the above synthetic route, the desired intermediate [A] can be prepared from the compound (I) of the invention by hydrolysis, reduction, oxidation and/or Wittig reaction and the like, depending on the type of the compound (I).

For example, a compound (I) wherein $R^1$ is 1-alkoxyalkyl group and $R^2$ is a group of formula:

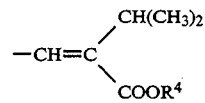

when treated with a mineral acid, an organic acid or a salt of a strong organic acid in an appropriate solvent, gives the directed Compound [A].

Examples of solvents to be used include protonic solvents such as methanol, ethanol and the like, aqueous solvent of a water-miscible solvent such as tetrahydrofuran, dioxane, acetic acid and the like, and two-layer solvents such as water and ethyl acetate, water and diethyl ether, water and dichloromethane and the like. Examples of mineral acids include hydrochloric acid, sulfuric acid and the like. Examples of organic acids include p-toluenesulfonic acid, methanesulfonic acid, and the like, and examples of salts of strong organic acids include p-toluenesulfonic acid pyridinium salt and the like. A catalytic amount to about 2 mol equivalent of a mineral acid, organic strong acid or a salt of a strong organic acid can be used.

The reaction can be conducted at temperature from about $-70°$ to about 100° C., preferably from about $-20°$ to about 50° C. Under these conditions, the reaction is generally complete in the period from about 5 minutes to about 2 days.

The thus obtained Compound [A], when treated according to the above-mentioned synthetic route 1 for sarcophytol A, gives the final product sarcophytol A via various intermediates as shown below.

COMPOUND [B]

Compound [B] can be prepared by halogenating Compound [A] without allyl rearrangement. Such a reaction can be carried out by reacting 1.0 to 10 mol equivalent of carbon tetrahalide in the presence of 1.0 to 10 mol equivalent of triphenylphosphine at temperature from room temperature to 100° C. over a period of 1 to 8 hours in an inert solvent such as acetonitrile or the like. In case of chlorination, carbon tetrachloride can be used as a solvent. Alternatively, it can be carried out by reacting 1.0 to 10 mol equivalent of methanesulfonyl chloride together with a metal halide and $\gamma$-collidine at temperature from $-40°$ C. to room temperature over a period of 1 to 10 hours.

Compound [B] wherein X is $OSO_2R^6$ ($R^6$ is as defined above) can be prepared by reacting an alcohol [A] with 1.0 to 10 mol equivalent of sulfonyl chloride such as methanesulfonyl chloride, p-toluenesulfonyl chloride or the like, or sulfonyl anhydride such as trifluoromethanesulfonic anhydride or the like in the presence of 1.0 to 10 mol equivalent of amine such as triethylamine, pyridine or the like at temperature from $-40°$ C. to room temperature over a period of 1 to 10 hours in an ether solvent such as ethyl ether, tetrahydrofuran or the like or a halogen solvent such as methylene chloride, chloroform or the like.

COMPOUND [C]

Compound [C] can be prepared from Compound [B] by reducing just the ester group, which is carried out by reacting Compound [B] with 1.0 to 10 mol equivalent of a metal hydride such as dibutylaluminium hydride or the like, or a metal hydride complex such as lithium aluminium hydride or the like at temperature from about −70° to about 50° C. in an ether solvent such as ethyl ether, tetrahydrofuran or the like, or a hydrocarbon solvent such as benzene, toluene, hexane, heptane or the like.

COMPOUND [D]

Compound [D] can be prepared by treating the Compound [C] with 5 to 20 times by weight of a oxidizing agent such as powdered manganese dioxide, barium manganate or the like at temperature from about 0° to about 50° C. over a period of 1 to 50 hours in a solvent, for example, a halogen solvent such as methylene chloride, chloroform or the like, a hydrocarbon solvent such as hexane, heptane or the like, or ethyl ether, or ethyl acetate or the like.

COMPOUND [E]

Compound [E] wherein $R^7$ is trimethylsilyl group is prepared, for example, by treating Compound [D] obtained by the above-mentioned process with 1.0 to 10 mol equivalent of trimethylsilylnitrile in the presence of a catalytic amount of a catalyst such as metal cyanide 18-crown-6-ether complex, tetraalkylammonium cyanide or the like at temperature from −20° to 50° C. over a period of 30 minutes to 5 hours in a solvent such as methylene chloride, chloroform, ethyl acetate or the like, or without solvent.

The resultant product can be converted into cyanohydrin Compound [E] wherein $R^7$ is hydrogen by treating with 0.1-3 N aqueous mineral acid such as hydrochloric acid, sulfuric acid or the like at 0° C. to room temperature over a period of 5 minutes to 5 hours or by treating with a catalytic amount to 10 mol equivalent of tetraalkylammonium salt such as tetrabutylammonium fluoride or the like at temperature from −20° C. to room temperature in a solvent such as tetrahydrofuran, dioxane or the like.

Compound [E] in which $R^7$ is 1-ethoxyethyl group can be prepared by reacting said cyanohydrin with 1.0 to 10 mol equivalent of ethyl vinyl ether in the presence of a catalytic amount of mineral acid such as hydrochloric acid, sulfuric acid or the like, an organic strong acid such as p-toluenesulfonic acid or a salt of strong acid such as p-toluenesulfonic acid pyridinium salt at temperature from −20° C. to room temperature over a period of 30 minutes to 5 hours in a solvent such as ethyl ether, ethyl acetate or the like.

COMPOUND [F]

Compound [F] in which $R^7$ is trimethylsilyl or 1-ethoxyethyl group can be prepared by reacting Compound [E] in which $R^7$ is trimethylsilyl or 1-ethoxycarbonyl group with 1.0 to 10 mol equivalent of a base such as lithium diisopropylamide, lithium bis-(trimethylsilyl) amide, sodium hydride or the like at temperature from about −70° to about 100° C. over a period of 5 minutes to 10 hours in an ether solvent such as ethyl ether, tetrahydrofuran or the like, an aromatic hydrocarbon solvent such as benzene, toluene or the like or a saturated hydrocarbon solvent such as n-hexane, n-heptane or the like.

Further, Compound [F] in which $R^7$ is hydrogen atom can be prepared by treating the resulting compound with 0.1-3 N aqueous mineral acid such as hydrochloric acid, sulfuric acid or the like at temperature from about 0° C. to room temperature over a period of 5 minutes to 5 hours in a solvent such as tetrahydrofuran, methanol or the like or by treating with a catalytic amount to 10 mol equivalent of tetraalkylammonium salt such as tetrabutylammonium fluoride at temperature from about −20° C. to room temperature in a solvent such as tetrahydrofuran, dioxane or the like.

COMPOUND [G]

The ketone, namely Compound [G], can be prepared from Compound [F], by treating a solution of Compound [F] wherein $R^7$ is hydrogen atom in an organic solvent such as ethyl ether, ethyl acetate or the like with aqueous sodium bicarbonate at temperature from about 0° C. to room temperature over a period of 5 minutes to 5 hours, or by treating Compound [F] wherein $R^7$ is trimethylsilyl group with a catalytic amount to 10 mol equivalent of an alkylammonium fluoride such as tetrabutylammonium fluoride in a solvent such as aqueous tetrahydrofuran, dioxane or the like.

SARCOPHYTOL A

Sarcophytol A can be prepared by reacting Compound [G] with 1.0 to 10 mol equivalent of a metal hydride such as diisobutylaluminum hydride or the like or a metal complex such as lithium aluminum hydride or the like at temperature from about −70° to about 50° C. over a period of 5 minutes to 5 hours in an ether solvent such as ethyl ether, tetrahydrofuran or the like, an aromatic hydrocarbon solvent such as benzene, toluene or the like or a saturated hydrocarbon solvent such as n-hexane, n-heptane or the like.

Further, sarcophytol A in native form shown below can be prepared by subjecting ketone Compound [G] to asymmetric reduction with an asymmetrically modified metal hydride or metal hydride complex.

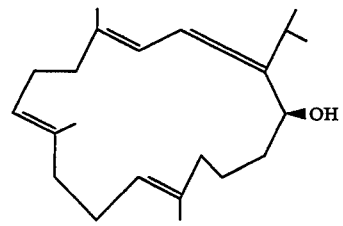

Sarcophytol A in native form

Examples of asymmetrically-modifying reagents used for preparing asymmetrically-modified metal hydride or metal hydride complex, which are used in the asymmetric reduction, include asymmetric amino alcohols prepared by converting carboxyl group of optically-active amino acid such as L- or D-proline, valine or the like into substituted alcohol group or substituted amino group [Bull. Soc.Chim. Belg. 97: 691 (1988); J. Chem. Soc. Perkin I 1673: (1983)]; asymmetric diamines [Bull. Chem. Soc. Japan 51: 1869 (1978); Tetrahedron 37: 4111 (1981)], asymmetric alkaloids such as L- or D-methylephedrine and the like [Chem. Pharm. Bull. 31: 837 (1983)]; and (S)- or (R)-1,1'-bis-2-naphtol and the like.

Examples of metal hydrides or metal hydride complexes include diisobutylaluminium hydride, lithium aluminium hydride, sodium borohydride and the like. An asymmetric reducing reagent can be prepared by reacting a metal hydride or metal hydride complex with 0.1 to 5 mol equivalent, preferably 0.5 to 1.5 mol equivalent of the above-mentioned asymmetrically-modifying reagent, optionally in the presence of an additive such as alkyl-substituted aniline, substituted aminopyridine, stannous chloride or the like at temperature from −50° to 50° C., preferably from −20° C. to room temperature over a period of 10 minutes to 5 hours in an appropriate solvent to obtain a coordinated complex of said asymmetrically-modifying reagent and metal hydride or metal hydride complex. Examples of appropriate solvents include ether solvents such as diethyl ether, tetrahydrofuran and the like and hydrocarbon solvents such as benzene, toluene, n-hexane and the like. A halogen solvent such as dichloromethane and chloroform is also available in case metal hydride is used. Illustrative combinations are listed in the Table 4 below.

TABLE 4

| metal hydride or hydride complex | asymmetric modifying reagent | additive |
|---|---|---|
| LiAlH₄ | (structure: Ph-CH(OH)-CH(Me)-NMe₂, positions 1,2) | H₅C₂N-H-Ph |
| LiAlH₄ | (pyrrolidine-CH-NH-Ph structure) | — |
| LiAlH₄ | (pyrrolidine-CH-NH-Ar(Me,Me) structure) | — |
| HAl(i-Bu)₂ (DIBAL) | (N-Me pyrrolidine-CH-N-piperidine structure) | SnCl₂ |
| BH₃ | (Ph,Ph oxazaborolidine with Me) | — |
| BH₃ | (Ph,Ph oxazaborolidine with H) | — |

Although the amount of the asymmetric reducing reagent to be reacted with the macrocyclic ketone shown by the structure [G] is not critical, it is preferable to use 1 to 2 mol equivalent of asymmetric reducing reagent for the ketone considering the recovery of unreacted starting materials and yield of the product. The reaction is usually conducted at temperature from −150° to 100° C., preferably from −100° C. to room temperature over a period of 10 minutes to 5 hours in the same solvent as that used for the preparation of the asymmetric reducing reagent. No regularity can be found between the absolute configuration of the product sarcophytol A ( its native form is expressed by $I_R$ and non-native form $I_S$ as shown below) and that of the asymmetric reducing reagent, which is attributable to the original compound in L- or D-form. The absolute configuration of the product varies depending on the combination of the asymmetric reducing reagent and metal hydride or metal hydride complex.

The by-product of the present method, sarcophytol A in non-native form of formula:

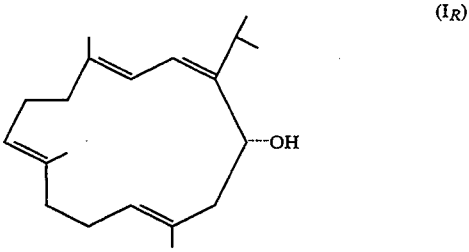

($I_R$)

, when treated under the conventional epimerization reaction for hydrokyl group, can be easily converted into the optically-active sarcophytol A ($I_S$) in native form after the inversion.

As can be seen from the above, an intermediate [A] is obtainable efficiently by the use of the compound (I) of the present invention. Thus, an industrially advantageous synthetic route for preparing sarcophytol A can be established by the use of the compound of the present invention, which demonstrates that said compound is highly useful and important for the attainment of the purpose of the invention.

Following Examples are provided for purpose of illustration only and are not to be constued as limiting the scope of the invention in any way.

EXAMPLE 1

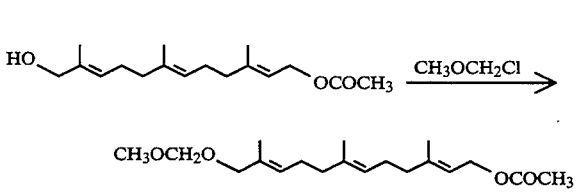

To a solution of 12-acetoxy-2,6,10-trimethyl-2,6,10-dodecatrien-1-ol (170 mg, 0.61 mmol) in dichloromethane (4 ml) were added chloromethyl methyl ether (92 μl, 1.21 mmol) and triethylamine (0.25 ml, 1.80 mmol), and the mixture was stirred at room temperature for 4 hours. Saturated aqueous sodium bicarbonate (5 ml) and ether (20 ml) were added to the reaction mixture, and the organic layer was separated. The aqueous layer was extracted with ether (20 ml). The combined ether layer was dried over Na₂SO₄ and evaporated to dryness in vacuo to give 12-acetoxy-2,6,10-trimethyl-2,6,10-dodecatriene 1-(methoxymethyl) ether (184 mg, 93%).

IR(film)cm⁻¹; 2950, 1745, 1235, 1050, 1030.

¹H NMR(CDCl₃, 250 MHz)δ ppm; 1.60, 1.67, 1.70(s, each 3H, 3CH₃C=CH), 1.95-2.25(m, 8H, 2x—CH₂—C=CH—CH₂—), 2.05(s, 3H, COCH₃), 3.37(s, 3H, CH₃O), 3.92(s, 2H, OCH₂CCH₃)=C), 4.50-4.70(m, 4H, OCH₂O, CH₂OAc), 5.10, 5.34, 5.42(each m, each 1H, —C=CH—CH₂).

EXAMPLE 2

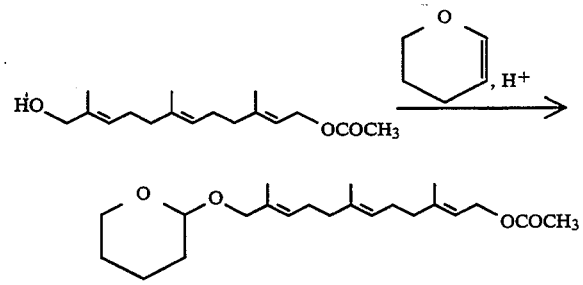

To a solution of 12-acetoxy-2,6,10-trimethyl-2,6,10-dodecatriene (180 mg, 0.64 mmol) in dichloromethane (4 ml) were added dihydropyran (88 μl, 0.96 mmol) and a trace amount of p-toluenesulfonic acid, and the mixture was stirred at room temperature for one hour. Saturated aqueous sodium bicarbonate (5 ml) and ether (20 ml) were added to the reaction mixture and mixed well. The organic layer was separated, and the aqueous layer was extracted with ether (20 ml). The extract was dried over Na$_2$SO$_4$ and evaporated to dryness in vacuo to give 12-acetoxy-2,6,10-trimethyl- 2,6,10-dodecatriene 1-(2-tetrahydropyranyl) ether (222 mg, 95%).

IR(film)cm$^{-1}$; 2950, 2880, 1745, 1440, 1380, 1235, 1175, 1120, 1080, 1023, 970, 908, 870, 807.

$^1$H NMR(CDCl$_3$, 250 MHz)δ ppm; 1.60, 1.66, 1.71(each s, each 3H, CH$_3$C=CH), 1.45–1.90(m, 6H, OCH$_2$CH$_2$CH$_2$CH$_2$CH(O)), 2.05(s, 3H, CH$_3$COO), 1.95-2.25(m, 8H, 2x—C=CHCH$_2$CH$_2$—), 3.48-3.58(m, 1H, —OCHaHbCH$_2$—), 3.84, 4.10(2d, J=11.8 Hz, 2H, —OCH$_2$C=CH—), 3.80-3.96(m, 1H, —OCHaHbCH$_2$—), 4.52-4.65(m, 3H, CH$_2$OCOOCH$_3$, —OCHO—), 5.28-5.47(m, 2H, 2x—CH=C—).

EXAMPLE 3

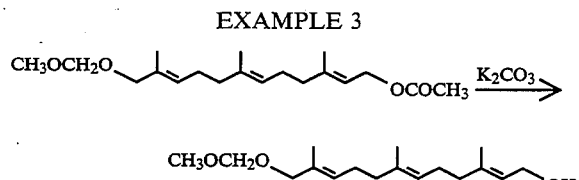

A mixture of 12-acetoxy-2,6,10-trimethyl-2,6,10-dodecatriene 1-(methoxymethyl) ether (125 mg, 0.385 mmol) and potassium carbonate (120 mg, 0.868 mmol) in a methanol/water (4:1) solvent (5 ml) was stirred at room temperature for one hour. After addition of saturated aqueous sodium chloride (5 ml), the reaction mixture was extracted with ether (20 ml×2). The organic extract was dried over Na$_2$SO$_4$ and evaporated to dryness in vacuo. The resultant residue was purified with silica gel chromatography to give 12-hydroxy-2,6,10-trimethyl-2,6,10-dodecatriene 1-(methoxymethyl) ether (100 mg, 92%).

IR(film)cm$^{-1}$; 3450, 2950, 1450, 1385, 1155, 1103, 1058.

$^1$H NMR(CDCl$_3$, 250 MHz)δ ppm; 1.61, 1.66, 1.68(each s, each 3H, CH$_3$C=CH), 1.98-2.25(m, 8H, 2x—C=CH—CH$_2$CH$_2$—), 3.38(s, 3H, CH$_3$O), 3.93(brs, 2H, CH$_2$OCH$_2$), 4.14(d, J=6.8 Hz, 2H, —C=CHCH$_2$OH), 4.62(s, 2H, CH$_3$OCH$_2$O), 5.11(brt, J=6.1 Hz, 1H, C=CH), 5.41(brt, J=6.8 Hz, 2H, 2xC=CH).

EXAMPLE 4

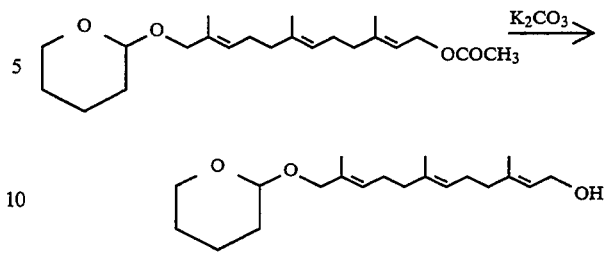

A mixture of 12-acetoxy-2,6,10-trimethyl-2,6,10-dodecatriene 1-(2-tetrahydropyranyl) ether (120 mg, 0.329 mmol) and potassium carbonate (220 mg, 1.59 mmol) in a methanol/water (4:1) solvent (5 ml) was stirred at room temperature for one hour. Saturated aqueous sodium bicarbonate (5 ml) was added to the reaction mixture, and the product was extracted with ether (20 ml×2). The organic extract was dried over Na$_2$SO$_4$ and evaporated to dryness to remove the solvent. The resultant residue was purified with alumina column chromatography to give 12-hydroxy-2,6,10-trimethyl-2,6,10-dodecatriene 1-(2-tetrahydropyranyl) ether (95 mg, 90%).

IR(film)cm$^{-1}$; 3430, 2960, 2890, 1445, 1385, 1203, 1120, 1080, 1025.

1H MNR(CDCl$_3$, 250 MHz)δ ppm; 1.60, 1.66, 1.68(each s, each 3H, CH$_3$C=CH—), 1.45–1.95(m, 6H,—OCH$_2$CH$_2$CH$_2$CH$_2$CH(O)), 195-2.26(m, 8H, 2x—C=CH—CH$_2$CH$_2$—), 3.44-3.57, 3.78-3.96, 4.03-4.22(m, 6H, 3xCH$_2$O), 4.60(brt, J=3.3 Hz, 1H, —O-CHO—), 5.12(brt, J=6.0 Hz, 1H, —C=CH—), 5.41(brt, J=6.6 Hz, 2H, 2x—C=CH—).

EXAMPLE 5

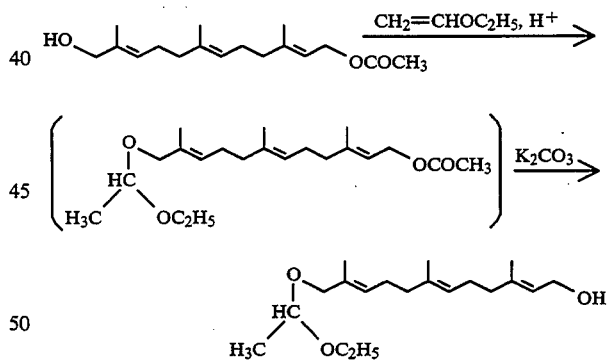

To an ice-cooled solution of 12-acetoxy-2,6,10-trimethyl-2,6,10-dodecatrien-1-ol (180 mg, 0.64 mmol) in dichloromethane (4 ml) were added ethyl vinyl ether (100 μl, 1.05 mmol) and a trace amount of p-toluenesulfonic acid. The mixture was gradually warmed up to room temperature and stirred additional 30 minutes. Saturated aqueous sodium bicarbonate (5 ml) was added to the reaction mixture, and the reaction product was extracted with ether (20 ml×2). The organic extract was dried over Na$_2$SO$_4$ and evaporated to dryness in vacuo to remove the solvent. The resultant crude product was purified with alumina column chromatography to give 12-hydroxy, 2,6,10-trimethyl-2,6,10-decatriene 1-(ethoxyethyl) ether (170 mg, 81%).

IR(film)cm$^{-1}$; 3450, 3000, 2950, 1445, 1385, 1133, 1100, 1090, 1060, 1025.

¹H NMR(CDCl₃, 250 MHz)δ ppm; 1.21(t, J=7.1 Hz, 3H, CH₃CH₂O), 1.31(d, J=5.3 Hz, 3H, CH₃CHO), 1.60, 1.66, 1.68(each s, each 3H, CH₃—C=CH—), 1.95-2.25(m, 8H, 2x—C=CH—CH₂CH₂—), 3.42-3.73(m, 2H, OCH₂CH₃), 3.84, 3.97(each d, J=11.5 Hz, each 2H, OCH₂C=CH), 4.14(d, J=6.8 Hz, 2H, CH₂OH), 4.70(q, J=5.3 Hz, 1H, CH(O)CH₃), 5.12(brt, J=6.0 Hz, 1H, —CH=C—), 5.41(m, 2H, 2x—CH=C—).

EXAMPLES 6-7

The procedures disclosed in Examples 3-5 were repeated except that 12-acetoxy-2,6,10-trimethyl-2,6,10-dodecatriene 1-(acetoxy) ether or 12-acetoxy-2,6,10-trimethyl-2,6,10-dodecatriene 1-(benzoyl) ether were employed as starting materials to give 12-hydroxy-2,6,10-trimethyl-2,6,10-dodecatriene 1-(acetoxy) ether and 12-hydroxy-2,6,10-trimethyl-2,6,10-dodecatriene 1-(benzoyl) ether.

EXAMPLE 8

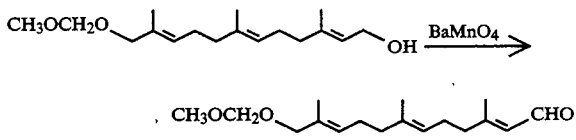

To a solution of 12-hydroxy-2,6,10-trimethyl-2,6,10-dodecatriene 1-(methoxymethyl) ether (100 mg, 0.354 mmol) dissolved in dichloromethane (8 ml) was added barium permanganate (2.00 g, 7.8 mmol) and the mixture was stirred at room temperature for 30 hours. The reaction mixture was filtered through celite, and the filtrate was evaporated in vacuo to remove the solvent. The residue was purified with silica gel column chromatography to give 11-formyl-2,6,10-trimethyl-2,6,10-undecatriene 1-(methoxymethyl) ether (95 mg, 96%).

IR(film)cm⁻¹; 2950, 1675, 1450, 1385, 1198, 1157, 1120, 1105, 1050, 925, 850.

¹H NMR(CDCl₃, 250 MHz)δ ppm; 1.57, 1.62, 2.13(each s, each 3H, CH₃C=CH—), 1.93-2.30(m, 8H, 2x—C=CH—CH₂—CH₂—), 3.33(s, 3H, CH₃O), 3.88(s, 2H, —OCH₂C=CH—), 4.57(s, 2H, —OCH₂O—), 5.06, 5.36(each m, each 1H, —C=CH—CH₂—), 5.84(d, J=8.2 Hz, 1H, —C=CH—CHO ), 9.96(d, J=8.2 Hz, 1H, —C=CH—CHO).

EXAMPLE 9

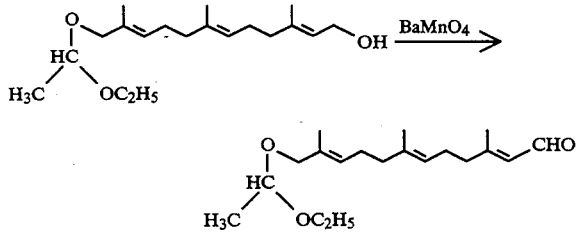

To a solution of 12-hydroxy-2,6,10-trimethyl-2,6,10-dodecatriene 1-(ethoxyethyl) ether (120 mg, 0.368 mmol) dissolved in dichloromethane (10 ml) was added barium permanganate (2.40 g, 9.36 mmol) and the mixture was stirred at room temperature for 30 hours. The reaction mixture was filtered through sellaite, and the filtrate was evaporated in vacuo to remove the solvent to give 11-formyl-2,6,10 -trimethyl-2,6,10-undecatriene 1-(ethoxyethyl) ether (112 mg, 94%).

IR(film)cm⁻¹; 2990, 2940, 2870, 1675, 1445, 1380, 1195, 1125, 1090, 1060, 1030.

¹H NMR(CDCl₃, 250 MHz)δ ppm; 1.21(t, J=7.0 Hz, 3H, CH₃CH₂O), 1.32(d, J=5.3 Hz, 3H, CH₃CH(O)), 1.61, 1.65, 2.17(each s, each 3H, CH₃C=CH), 1.95-2.30(m, 8H, 2x—C=CH—CH₂CH₂—), 3.42-3.70(m, 2H, CH₃CH₂O), 3.84, 3.96(each d, J=11.3 Hz, each 1H, —OCH₂C=CH—), 4.70(q, J=5.3 Hz, 1H, CH₃CH(O)), 5.10(m, 1H, —CH₂C=CH—CH₂), 5.39(brt, J=6.8 Hz, 1H, —OCH₂C=CH—), 5.88(d, J=8.0 Hz, 1H, —C=CH—CHO), 10.00(d, J=8.0 Hz, 1H, CHO).

EXAMPLE 10

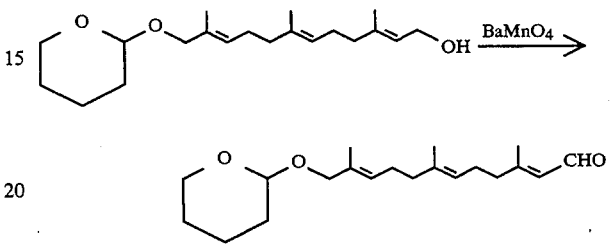

To a solution of 12-hydroxy-2,6,10-trimethyl-2,6,10-dodecatriene 1-(2-tetrahydropyranyl) ether (90 mg, 0.279 mmol) dissolved in dichloromethane (8 ml) was added barium permanganate (1.43 g, 5.58 mmol) and the mixture was stirred at room temperature for 24 hours. The reaction mixture was filtered through sellaite, and the filtrate was evaporated in vacuo to remove the solvent to give 11-formyl-2,6,10-trimethyl-2,6,10-undecatriene 1 -(2-tetrahydropyranyl) ether (86.7 mg, 97%).

IR(film)cm⁻¹; 2960, 2870, 1680, 1445, 1385, 1202, 1122, 1080, 1040, 1028, 980, 910, 872, 818.

¹H NMR(CDCl₃, 250 MHz)δ ppm; 1.61, 1.65, 2.17(each s, each 3H, CH₃C=CH—), 1.46-1.87(m, 6H, —OCH₂CH₂CH₂CH₂CH(O)), 1.87-2.33(m, 8H, 2x—C=CH—CH₂CH₂—), 3.40-3.57, 3.77-3.94(m, 2H, —CH₂CH₂O—), 3.83, 4.09(2d, J=11.6 Hz, 2H, —OCH₂C=CH—), 4.60(brs, 1H, —OCHO—), 5.09, 5.40(each m, each 1H, 2xC=CH—), 5.88(d, J=8.1 Hz, 1H, C=CH—CHO), 10.02(d, J=8.1 Hz, 1H, C=CH—CHO).

EXAMPLES 11-12

The procedures disclosed in Examples 8-10 were repeated except that 12-hydroxy-2,6,10-trimethyl-2,6,10-dodecatriene 1-(acetoxy) ether or 12-hydroxy-2,6,10-trimethyl-2,6,10-dodecatriene 1-(benzoyl) ether was employed as starting materials to give 11-formyl-2,6,10-trimethyl-2,6,10-undecatriene 1-(acetoxy) ether and 11-formyl-2,6,10-trimethyl-2,6,10-undecatriene 1-(benzoyl) ether.

EXAMPLE 13

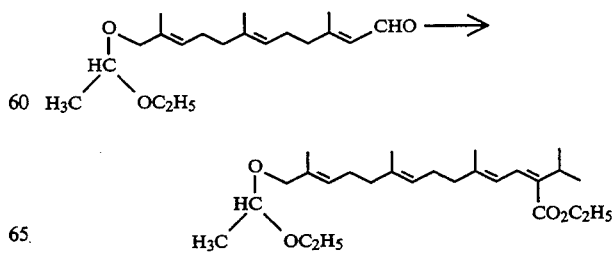

A solution of ethyl 2-(diethylphosphono)-3-methylbutanoate (4.0 g, 15 mmol) in THF (50 ml) was stirred in a cooling bath at −78° C. under nitrogen atmosphere. To the solution was gradually added n-butyl lithium (14.9 mmol) in hexane (10 ml), and the mixture was stirred at −78° C. for 15 minutes. To the reaction mixture was dropwise added over 10 minutes 11-formyl-2,6,10-trimethyl-2,6,10-undecatriene 1-(1-ethoxyethyl) ether (4.54 g, 14.0 mmol) in THF (7 ml), and the mixture was gradually warmed to room temperature over 2.5 hours. After addition of water (5 ml), most of THF was removed by evaporation in vacuo, and the residue was dissolved in a mixture of ether (50 ml) and water (50 ml). The organic layer was separated, dried over Na$_2$SO$_4$, and condensed, and the resultant residue was subjected to alumina column chromatography to give the aimed 13-(ethoxycarbonyl)-13-(1-methylethyl)-2,6,10-trimethyl-2,6,10-tridecatetraen 1-(ethoxyethyl) ether (5.42 g, 92%).

IR(film)cm$^{-1}$; 3000, 2950, 1710, 1450, 1385, 1240, 1200, 1140, 1095, 1045.

$^1$H NMR(CDCl$_3$, 250 MHz)δ ppm; 1.11(d, J=6.8 Hz, 6H, (CH$_3$)$_2$CH, 1.17-1.26(m, 3H, CH$_3$CHO—), 1.27-1.37(m, 6H, CH$_3$CHO—, —COOCH$_2$CH$_3$), 1.57-1.90(m, 9H, 3xCH$_3$C=CH—), 1.85-2.30(m, 8H, 2x—C=CH—CH$_2$—CH$_2$—), 2.80, 3.06(hep, J=6.8 Hz, 1H, (CH$_3$)$_2$CH), 3.40-3.72(m, 2H, CH$_3$CH$_2$O—), 3.80-4.07(m, 2H, —OCH$_2$C=CH—), 4.15-4.30(m, 2H, —COOCH$_2$CH$_3$), 4.70(q, J=5.3 Hz, 1H, CH$_3$CH(O)), 5.13, 5.40(each m, each 1H, 2x—C=CH—), 6.22, 6.56, 7.32(m, 1H, —C=CH—CH=C—).

EXAMPLES 14-15

The procedures disclosed in Example 13 was repeated except that 11-formyl-2,6,10-trimethyl-2,6,10-undecatriene 1-(methoxymethyl) ether or 11-formyl-2,6,10-trimethyl-2,6,10-undecatriene 1-(2-tetrahydropyranyl) ether were employed as starting materials to give 13-(ethoxycarbonyl)-13-(1-methylethyl)--2,6,10-trimethyl-2,6,10-tridecatetraene 1-(methoxymethyl) ether and 13-(ethoxycarbonyl)-13-(1-methylethyl)-2,6,10-trimethyl-2,6,10-tridecatetraene 1-(2-tetrahydropyranyl) ether.

REFERENCE EXAMPLE 1

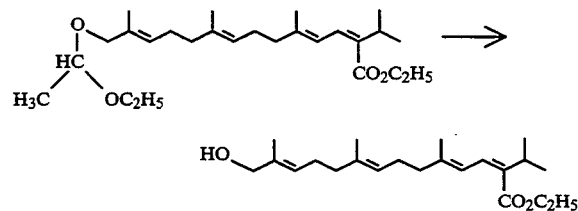

To a solution of 13-ethoxycarbonyl-2,6,10,14-tetramethyl-2,6,10,12-tetradecatetraene 1-(1-ethoxyethyl) ether (174 mg, 0.50 mmol) in methanol (5 ml) was added pyridinium p-toluenesulfonate (13 mg, 0.05 mmol), and the mixture was stirred at room temperature for 4 hours. To the reaction mixture was added saturated aqueous sodium chloride (10 ml) and ether (20 ml), and the organic layer was separated. The aqueous layer was extracted with ether (20 ml). The organic layer was washed with saturated aqueous sodium chloride (10 ml), dried over Na$_2$SO$_4$, evaporated in vacuo to remove the solvent. The residue was subjected to silica gel column chromatography to give 13-ethoxycarbonyl-2,6,10,14-tetramethyl-2,6,10,12-tetradecatrien-1-ol (164 mg, 94%).

REFERENCE EXAMPLE 2

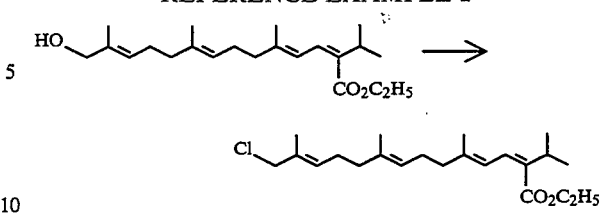

To a solution of ethyl 14-hydroxy-2-(1-methylethyl)-5,9,13-trimethyl-2,4,8,12-tetradecatetraenoate (713 mg, 2.03 mmol) in dry carbon tetrachloride (2 ml) was added triphenylphosphine (787 mg, 3.00 mmol), and the mixture was heated under reflux with stirring for 2 hours. After confirmation of disappearance of the starting material, the mixture was cooled to room temperature, and n-hexane was added thereto. Insoluble triphenylphosphine oxide was filtered and washed with n-hexane. The liltrate and the washing were combined and condensed. The resultant residue was added to a small amount of n-hexane, filtered, and washed to remove the residual triphenylphosphine oxide. The filtrate and the washing were combined and condensed to give as a residue the aimed ethyl 14-chloro-2-(1-methylethyl)-5,9,13-trimethyl-2,4,8,12-tetradecatetraenoate. The product was used in the subsequent reaction without purification.

IR(film)cm$^{-1}$; 2960, 2940, 2870, 1710, 1635, 1445, 1385, 1230, 1195, 1145, 1050.

NMR(CDCl$_3$, 250 MHz)δ ppm; 1.09(d, J=6.9 Hz, 6H, —CH(CH$_3$)$_2$), 1.31(t, J=7.1 Hz, 3H, —CH$_2$CH$_3$), 1.57, 1.70, 1.80(each bs, each 3H, —C=CCH$_3$), 1.9-2.2(m, 8H, —CH$_2$CH$_2$—), 2.78(hep, J=6.9 Hz, 1H, CH(CH$_3$)$_2$), 3.98(bs, 2H, —CH$_2$Cl), 4.23(q, J=7.1 Hz, 2H, —CH$_2$CH$_3$), 5.1(m, 1H, —C=CHCH$_2$—), 5.47(bt, J=6.5 Hz, —C=CHCH$_2$—), 6.53, 6.54(each bd, J=12.0 Hz, each 1H, —C=CH—CH=C—).

REFERENCE EXAMPLE 3

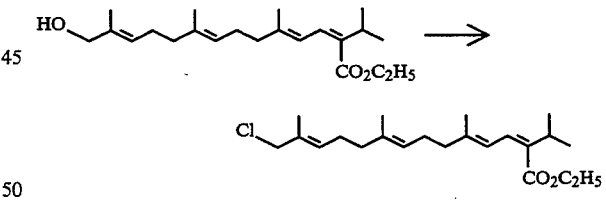

To a mixture of ethyl 14-hydroxy-2-(1-methylethyl)-5,9,13-trimethyl-2,4,8,12-tetradecatetraenoate (71.0 mg, 0.20 mmol), τ-collidine (26.7 mg, 0.22 mmol), lithium chloride (8.5 mg, 0.20 mmol), and dimethylformamide (1 ml) was added with stirring methanesulfonyl chloride (25.2 mg, 0.22 mmol) on an ice-water bath and under nitrogen atmosphere. The stirring was continued at the same temperature for 5 hours. After confirmation of disappearance of the starting material, water and ether were added to the reaction mixture. The organic layer was separated, washed with water, dried over MgSO$_4$, and condensed to give a residue, which was then subjected to silica gel column chromatography (solvent: n-hexane/ethyl acetate (10:1)). Relevant fractions gave the aimed ethyl 14-chloro-2-(1-methylethyl)-5,9,13-trimethyl-2,4,8,12-tetradecatetraenoate (64.6 mg, 86%).

REFERENCE EXAMPLE 4

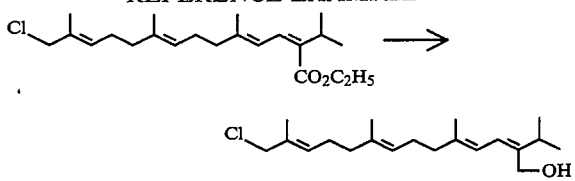

Ethyl 14-chloro-2-(1-methylethyl)-5,9,13-trimethyl-2,4,8,12-tetradecatetraenoate (670 mg, 1.81 mmol) was dissolved in dry toluene (20 ml) under argon atmosphere. To the solution cooled on an ethanol-dry ice bath was added with stirring 1M diisopropyl aluminium hydride in toluene (4 ml). After 30 minutes, disappearance of the starting material was confirmed. Water (1.5 ml) was added to the reaction mixture, the cooling bath was removed, and the stirring was continued. After further stirring with addition of $MgSO_4$ as a drying agent, the mixture was filtered and condensed. The resulting residue was subjected to silica gel column chromatography (solvent: n-hexane/ethyl acetate (12:1)), and relevant fractions gave 14-chloro-2-(1-methylethyl)-5,9,13-trimethyl-2,4,8,12-tetradecatetraen-1-ol (492 mg, 79%).

IR(film)cm$^{-1}$; 3360, 2980, 2940, 2890, 1445, 1385, 1265, 1010.

NMR(CDCl$_3$, 250 MHz)δ ppm; 1.06(d, J=6.8 Hz, 6H, —CH(CH$_3$)$_2$), 1.58, 1.70, 1.75(each bs, each 3H, —C=CCH$_3$), 1.9-2.2(m, 8H, —CH$_2$CH$_2$—), 2.47(hep, J=6.8 Hz, 1H, —CH(CH$_3$)$_2$), 3.98(bs, 2H, —CH$_2$Cl), 4.23(bs, 2H, —CH$_2$OH), 5.09(m, 1H, —C=CHCH$_2$—), 5.47(bt, J=6.7 Hz, —C=CHCH$_2$—), 6.13, 6.16(each d, J=12.0 Hz, each 1H, —C=CH—CH=C—).

REFERENCE EXAMPLE 5

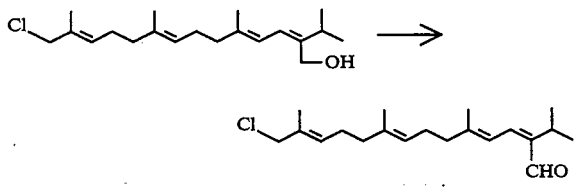

To a solution of 14-chloro-2-(1-methylethyl)-5,9,13-trimethyl-2,4,8,12-tetradecatetraen-1-ol (492 mg, 1.51 mmol), which was obtained in Reference Example 3, dissolved in methylene chloride (22 ml) was added barium manganate (8.5 g), and the mixture was stirred under argon atmosphere. After confirmation of disappearance of the starting material 8 hours later, the reaction mixture was filtered, and the filter cake was washed. The filtrate and the washing were combined and concentrated. The resultant residue was subjected to silica gel column chromatography (solvent: n-hexane/ethyl acetate (15:1)) for purification to give the aimed 14-chloro-2-(1-methylethyl)-5,9,13-trimethyl--2,4,8,12-tetradecatetraenal (468 mg, 95%).

IR(film)cm$^{-1}$; 2970, 2930, 2880, 1670, 1630, 1445, 1390, 1295, 1265, 1135.

NMR(CDCl$_3$, 250 MHz)δ ppm; 1.04(d, J=7.0 Hz, 6H, —CH(CH$_3$)$_2$), 1.59, 1.70(each bs, each 3H, —C=CCH$_3$), 1.87(d, J=1.3 Hz, 3H, —C=CCH$_3$), 1.9-2.2(m, 8H, —CH$_2$CH$_2$—), 2.89(hep, J=7.0 Hz, 1H, —CH(CH$_3$)$_2$), 3.98(bs, 2H, —CH$_2$Cl), 5.09(m, 1H, —C=CHCH$_2$—), 5.47(bt, J=6.5 Hz, 1H, —C=CHCH$_2$—), 6.82(d, J=12.0 Hz, 1H, —C=CH—CH=C(-CHO)—), 7.11(d, J=12.0 Hz, —C=CH—CH=C(-CHO)—), 10.27(s, 1H, —CHO).

REFERENCE EXAMPLE 6

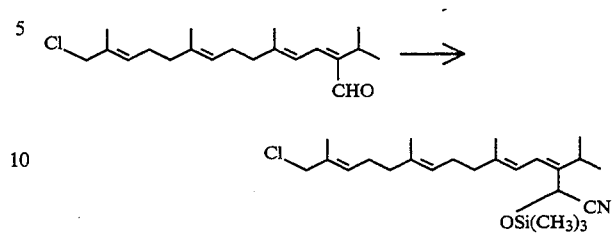

The above formyl compound, 14-chloro-2-(1-methylethyl)-5,9,13-trimethyl-2,4,8,12-tetradecatetraenal (640 mg, 2.0 mmol) was dissolved in trimethylsilylnitril (0.35 ml, 2.6 mmol). To the solution on an ice-water bath was added with stirring under argon atmosphere a trace amount of potassium cyanide/18-crown 6-ether complex. Two hours later, disappearance of the starting compound was confirmed. Excessive trimethylsilylnitrile was evaporated off to obtain crude 15-chloro-3-(1-methylethyl)-6,10,14-trimethyl-2-(trimethylsiloxy)-3,5,9,13-pentadecatetraenenitrile (647 mg, quantitative).

IR(film)cm$^{-1}$; 2960, 2930, 2880, 2320, 1445, 1255, 1080, 875, 845.

NMR(CDCl$_3$, 250 MHz)δ ppm; 1.11, 1.15(each d, J=6.9 Hz, each 3H, —CH(CH$_3$)$_2$), 1.60, 1.71, 1.77(each s, each 3H, —C=CCH$_3$), 1.9-2.2(m, 8H, —CH$_2$CH$_2$—), 2.64(hep, J=6.9 Hz, 1H, —CH(CH$_3$)$_2$,3.99(s, 1H, —CH$_2$Cl), 5.11(m, 1H, —C=CHCH$_2$—), 5.33(s, 1H, —CHCN), 5.48(bt, J=6.5 Hz, 1H, —C=CHCH$_2$—), 6.04, 6.25(each d, J=11.3 Hz, each 1H, —C=-CH—CH=C—).

REFERENCE EXAMPLE 7

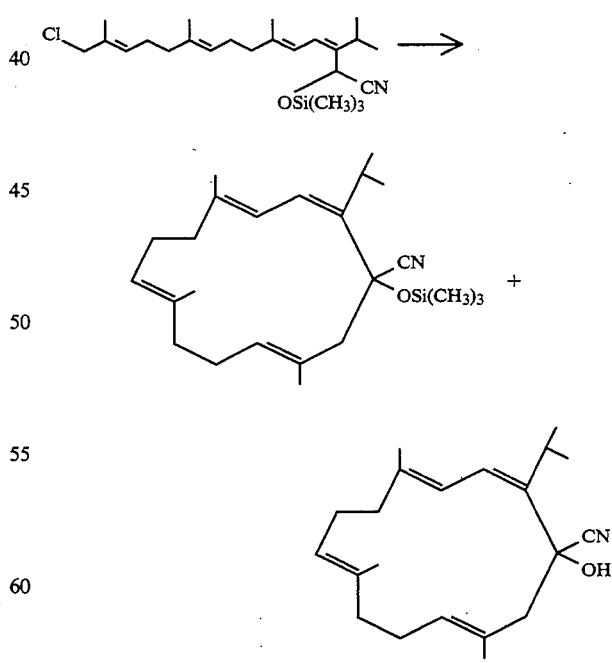

A solution of the crude cyanohydrine trimethylsilyl ether (647 mg, 2.00 mmol if it is 100% pure), which was obtained in Reference Example 6, in tetrahydrofuran (25 ml) was dropwise added with stirring at 50°-55° C. under argon atmosphere over 30 minutes to a solution of 1 M lithium bis(trimethylsilyl)amide in tetrahydrofuran, which had been diluted with 25 ml of tetrahydrofuran. After completion of the dropwise addition, the tetrahydrofuran was evaporated off in vacuo, and the residue was dissolved in ethyl ether (30 ml), and the solution was washed with cooled 1 N HCl, water, and then saturated aqueous sodium chloride. The organic layer was dried over MgSO4 and then concentrated to give a residue, which was then subjected to silica gel column chromatography (solvent: n-hexane/ethyl acetate=50:1-5:1) to obtain the aimed cyclized 2-(1-methylethyl)-5,9,13-trimethyl-1-trimethylsiloxy-2,4,8,12-cyclotetradecatetraen-1-carbonitrile (496 mg, 64%) and desilylated analogue (56 mg, 9%).

NMR Spectrum of 1-Trimethylsiloxy Compound

NMR(CDCl3, 250 MHz)δ ppm; 0.23(s, 9H, —Si(CH3)3), 1.09, 1.15(each d, J=6.7 Hz, each 3H, —CH(CH3)2), 1.50, 1.62(each bs, each 3H, —C=CCH3), 1.70(d, J=1.3 Hz, 3H, —C=CCH3), 2.0-2.2(m, 8H, —CH2CH2—), 2.51(hep, J=6.7 Hz, 1H, —CH(CH3)2), 2.55, 2.65(each d, J=14.2 Hz, each 1H, —CHa Hb CN—), 4.94(bt, J=6.1 Hz, 1H, —C=CHCH2—), 5.15(bt, J=5.6 Hz, 1H, —C=CHCH2—), 6.17, 6.44(each d, J=11.8 Hz, each 1H, —C=CH—CH=C—).

NMR Spectrum of 1-Hydroxy Compound

NMR(CDCl3, 250 MHz)δ ppm; 1.15, 1.19(each d, J=6.7 Hz, each 3H, CH(CH3)2), 1.55, 1.63, 1.69(each s, each 3H, CH3—C=C—), 1.94-2.35(m, 8H, CH2—C=C—), 2.51(hep, J=6.7 Hz, 1H, CH(CH3)2), 2.66, 2.73(each d, J=14.1 Hz, 2H, CHa Hb CCN), 2.89(brs, 1H, OH), 4.93, 5.24(each brt, J=5.3 Hz, each 1H, —C=CH—CH2), 6.22, 6.42(each d, J=11.1 Hz, each 1H, —C=CH—CH=C—).

REFERENCE EXAMPLE 8

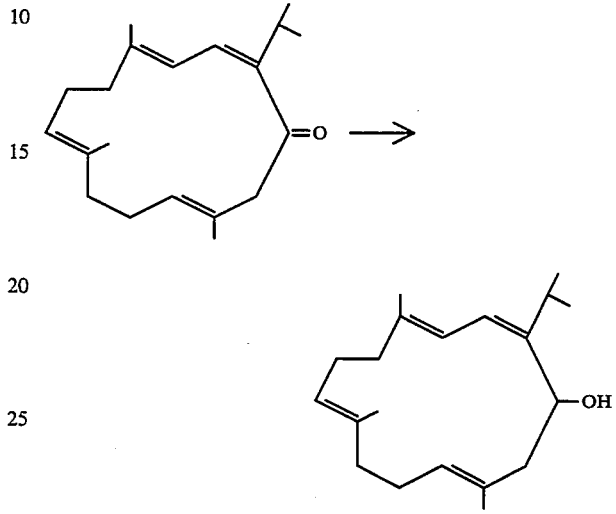

The above cyanohydrine trimethylsilyl ether compound, 2-(1-methylethyl)-5,9,13-trimethyl-1-trimethylsiloxy-2,4,8,12-cyclotetradecatetraen-1-carbonitrile (657 mg, 1.7 mmol) was dissolved in 10% aqueous tetrahydrofuran (10 ml). To the solution on an ice-water bath was added a solution of 1 M tetra n-butylammonium fluoride in tetrahydrofuran (0.02 ml), and the mixture was stirred and then allowed to stand at room temperature for 2 days. Most of the tetrahydrofuran was removed in vacuo and the residue was dissolved in ethyl ether. The ether layer was dried over MgSO4, filtered, concentrated, and subjected to silica gel column chromatography (solvent: n-hexane/ethyl acetate=30:1) to obtain the ketone compound, 2-(1-methylethyl)-5,9,13-trimethyl-2,4,8,12-cyclotetradecatetraen-1-one (411 mg, 85%).

REFERENCE EXAMPLE 9

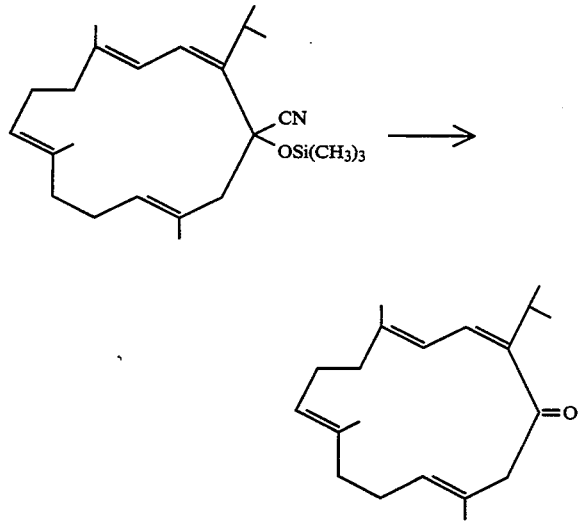

To the above ketone compound, 2-(1-methylethyl)-5,9,13-trimethyl-2,4,8,12-cyclotetradecatetraen-1-one (137 mg, 0.48 mmol) in dry toluene (2.5 ml) was dropwise added with stirring on a cooling bath at −70° C. a solution of 1 M diisobutyl aluminium hydride in toluene (0.6 ml). One hour later, disappearance of the starting material was confirmed. After addition of water (0.25 ml) and removal of the cooling bath, the reaction mixture was stirred, followed by drying over MgSO4, filtration, and concentration to give a residue, which was subjected to silica gel column chromatography (solvent: n-hexane/ethyl acetate=12:1) to obtain the aimed sarcophytol A (125 mg, 88%).

Reference Example 10

Lithium alumminium hydride (80.0 mg, 2.11 mmol) was added to diethyl ether (5 ml) under argon atmosphere, and the mixture was stirred. To the suspension was dropwise added at room temperature over 5 minutes a solution of (1R,2S)-(-)-N-methylephedrine (308 mg, 2.12 mmol) in diethyl ether (5 ml). After one hour reflux of the reaction mixture with stirring, N-ethylaniline (0.53 ml, 4.23 mmol) was dropwise added thereto over 5 minutes, and the mixture was refluxed with stirring additional one hour. The mixture was then cooled to −72° C., and a solution of the ketone compound (136 mg, 0.475 mmol) obtained in Reference Example 8 in diethyl ether (3 ml) was gradually added thereto, and the mixture was stirred for 6 hours at −72° C. After addition of 1N HCl (9 ml), the organic layer was separated, washed with 3N HCl (5 mlx2), and dried over Na2SO4. Removal of the solvent in vacuo gave a residue, which was then subjected to silica gel column chromatography to give optically active sarcophytol A (81 mg, 60%) and nonreacted ketone compound (51 mg, 37%).

Optical purity of the optically active sarcophytol A was determined to be 87% by means of high pressure liquid chromatography using a separation column for optical isomers, specifically CHIRALCELL OD (commercially available from Daisel Kagaku Kogyo), said analysis being referred to as "HPLC analysis using CHIRALCELL OD" hereinafter.

Reference Example 11

A solution of lithium aluminum hydride in diethyl ether (2.26 ml, 1.40 mmol, 0.62 M) was stirred under argon atmosphere. To the solution was dropwise added (S)-2-(anilinomethyl)pyrolidine (296 mg, 1.68 mmol) in diethyl ether (3 ml) at room temperature over 10 minutes. The reaction mixture was stirred at room temperature additional one hour and then cooled to −72° C. To the mixture was gradually added the ketone compound (162 mg, 0.56 mmol)in diethyl ether (5 ml), which had been prepared in Reference Example 8. After one hour stirring at −72° C., saturated aqueous sodium bicarbonate (1 ml) was added, and the mixture was stirred at room temperature for 10 minutes. After addition of 1N HCl (15 ml) and diethyl ether (20 ml), the organic layer was separated. The aqueous layer was extracted with diethyl ether (20 ml), and the extract was washed with saturated aqueous sodium chloride (20 ml), dried over Na2SO4, and evaporated in vacuo to remove the solvent. The resultant residue was subjected to silica gel column chromatography to obtain optically active sarcophytol A (126 mg, 78%).

Optical purity of the thus obtained sarcophytol A was 92% when measured by HPLC analysis using CHIRALCELL OD. $[\alpha]^{24}_D$: +209.9° (c=0.372, CHCl3)

Reference Example 12

A solution of lithium aluminium hydride in diethyl ether (2.94 ml, 2.0 mmol, 0.68 M) was stirred under argon atmosphere, and to the solution was gradually added (S)-2-(2,6-xylidinomethyl)pyrrolidine (490 mg, 2.4 mmol) at room temperature, and the mixture was stirred at room temperature for 2 hours. The reaction mixture was cooled to −74° C., and to the mixture was dropwise added over 10 minutes a solution of the ketone compound (69 mg, 0.24 mmol) in diethyl ether (3 ml), which had been prepared in Reference Example 8. After one hour stirring at −74° C., saturated aqueous sodium sulfonate (1 ml) was added, and the resultant mixture was stirred at room temperature for a while. After addition of diethyl ether (10 ml) and diluted HCl (20 ml), the organic layer was separated, and the aqueous layer was extracted with diethyl ether (20 ml). The extract was washed with saturated aqueous sodium chloride (20 ml), dried over Na2SO4, and evaporated in vacuo to remove the solvent to give a residue, which was subjected to silica gel column chromatography to obtain optically active sarcophytol A (61 mg, 88%).

Optical purity of the optically active sarcophytol A was 93% according to HPLC analysis using CHIRALCELL OD. $[\alpha]^{24}_D$: +204.4° (c=0.27, CHCl3)

Reference Example 13

A suspension of tin (II) chloride (382 mg, 2.01 mmol) and (R)-1-methyl-2-(piperidinomethyl)pyrrodine (366 mg, 2.01 mmol) in dichloromethane (6 ml) was cooled to −72° C. under argon atmosphere. To the suspension was added diisobutylaluminum hydride in toluene (1.0 mmol), and the mixture was stirred for ten minutes. To the mixture was gradually added at −72° C. a solution of the ketone compound (100 mg, 0.349 mmol) in dichloromethane (3 ml). The reaction mixture was stirred for 4 hours, and the stirring was continued at room temperature for 30 minutes after addition of saturated aqueous sodium chloride (3 ml). Resultant precipitates were filtered by the use of sellite, and the filtrate was dried over Na2SO4 and evaporated in vacuo to remove the solvent. The resultant residue was purified with silica gel column chromatography to give optically active sarcophytol A (79.2 mg, 79%).

Optical purity of the sarcophytol A thus obtained was 42% according to HPLC analysis using CHIRALCELL OD. $[\alpha]^{25}_D$: +101.9° (c=0.54, CHCl3)

Industrial Utility

As stated above, the compounds (I) of the present invention are very useful as intermediates for preparing sarcophytol A which possesses an anti-carcinogenic promotor activity and anti-tumor activity. Thus, the present invention provides a method suitable for industrial production of sarcophytol A.

What is claimed is:

1. An acyclic terpene compound of the formula (I):

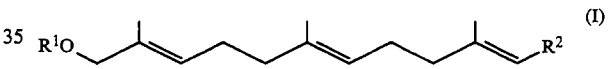

wherein $R^1$ is a hydrogen atom, 1-alkoxyalkyl group, tetrahydrofuryl group, tetrahydropyranyl group, benzoyl group or acetyl group; $R^2$ is a group of the formula —CHO or

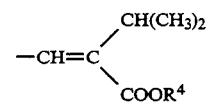

wherein $R^4$ is a C1 to C4 alkyl group; with the proviso that when $R^2$ is a group of the formula:

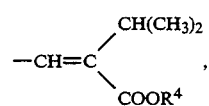

$R^1$ is not a hydrogen atom.

* * * * *